United States Patent
Peschka et al.

(10) Patent No.: US 10,085,638 B2
(45) Date of Patent: Oct. 2, 2018

(54) OPTICAL COHERENCE TOMOGRAPHY SYSTEM

(71) Applicant: CARL ZEISS MEDITEC AG, Jena (DE)

(72) Inventors: Martin Peschka, Aalen (DE); Xiaoxian Guo, Shanghai (CN); Alexandre R. Tumlinson, San Leandro, CA (US)

(73) Assignees: CARL ZEISS MEDITEC, INC., Dublin, CA (US); CARL ZEISS MEDITEC AG, Jena (DE)

( * ) Notice: Subject to any disclaimer, the term of this patent is extended or adjusted under 35 U.S.C. 154(b) by 418 days.

(21) Appl. No.: 14/908,256

(22) PCT Filed: Aug. 5, 2014

(86) PCT No.: PCT/EP2014/002149
§ 371 (c)(1),
(2) Date: Jan. 28, 2016

(87) PCT Pub. No.: WO2015/018514
PCT Pub. Date: Feb. 12, 2015

(65) Prior Publication Data
US 2016/0166147 A1     Jun. 16, 2016

(30) Foreign Application Priority Data
Aug. 7, 2013 (CN) .......................... 2013 1 0341427

(51) Int. Cl.
*A61B 3/18* (2006.01)
*A61B 3/00* (2006.01)
(Continued)

(52) U.S. Cl.
CPC ............ *A61B 3/185* (2013.01); *A61B 3/0091* (2013.01); *A61B 3/102* (2013.01); *A61B 3/117* (2013.01); *A61B 3/12* (2013.01); *A61B 3/1225* (2013.01)

(58) Field of Classification Search
CPC ....... A61B 3/185; A61B 3/102; A61B 3/0091; A61B 3/117; A61B 3/1225
See application file for complete search history.

(56) References Cited

U.S. PATENT DOCUMENTS

2007/0242222 A1   10/2007   Iwanaga et al.
2007/0291277 A1   12/2007   Everett et al.
(Continued)

FOREIGN PATENT DOCUMENTS

CN        1810202 A      8/2006
CN      101040776 A      9/2007
(Continued)

OTHER PUBLICATIONS

Office Action received for European Patent Application No. 14748123.8, dated Jul. 27, 2017, 6 pages.
(Continued)

*Primary Examiner* — Jack Dinh
(74) *Attorney, Agent, or Firm* — Morrison & Foerster LLP (57) ABSTRACT

An OCT system comprises an OCT scan module for retinal scanning and an add-on anterior segment scanning module which includes at least one anterior segment scan lens (11) and an add-on fixation target (15) which is used to maintain the viewing direction of the eye (6) under investigation while achieving anterior segment scanning. Because the anterior segment scan module added to the exterior of an existing OCT system for retinal scanning has an add-on fixation target (15), it is possible to maintain the viewing (Continued)

direction of the eye (6) under investigation while carrying out anterior segment scanning without adjusting the internal beam path of the OCT system, and the OCT system of the present invention can be adapted to patients with only one functioning eye.

23 Claims, 4 Drawing Sheets

(51) Int. Cl.
    *A61B 3/10*     (2006.01)
    *A61B 3/117*     (2006.01)
    *A61B 3/12*     (2006.01)

(56) References Cited

U.S. PATENT DOCUMENTS

| | | |
|---|---|---|
| 2008/0106696 A1 | 5/2008 | Buckland et al. |
| 2009/0141237 A1 | 6/2009 | Izatt et al. |
| 2011/0267583 A1 | 11/2011 | Hayashi |
| 2012/0140176 A1 | 6/2012 | Buckland et al. |
| 2013/0182219 A1 | 7/2013 | Numajiri et al. |

FOREIGN PATENT DOCUMENTS

| | | |
|---|---|---|
| CN | 102438505 A | 5/2012 |
| CN | 102551654 A | 7/2012 |
| CN | 203436316 U | 2/2014 |
| EP | 2347701 A1 | 7/2011 |
| JP | 6-237901 A | 8/1994 |
| JP | 10-272104 A | 10/1998 |
| JP | 11-225970 A | 8/1999 |
| JP | 2012-223435 A | 11/2012 |

OTHER PUBLICATIONS

Office Action received for Chinese Patent Application No. 201310341427.3, dated Jan. 4, 2016, 9 pages (3 pages of English Translation and 6 pages of Official copy).

International Preliminary Report on Patentability received for PCT Patent Application No. PCT/EP2014/002149, dated Feb. 18, 2016, 8 pages.

International Search Report and Written Opinion received for PCT Patent Application No. PCT/EP2014/002149, dated Nov. 12, 2014, 11 pages.

Heideberg Engineering GMBH, "Spectralis Anterior Segment Module—The Perfect Acquisition", available at <https://www.heidelbergengineering.com/international/wp-content/uploads/2012/03/SPECTRALIS-ASM_How-to-acquire-perfect-image_EN_web.pdf>, Mar. 2012, 8 pages.

OPTICAL COHERENCE TOMOGRAPHY SYSTEM

CROSS-REFERENCE TO RELATED APPLICATIONS

This application is a National Phase application under 35 U.S.C. § 371 of International Application No. PCT/EP2014/002149, filed Aug. 5, 2014, which claims priority to Chinese Patent Application No. 201310341427.3, filed Aug. 7, 2013, the disclosure of each of which is hereby incorporated herein by reference in its entirety.

TECHNICAL FIELD

The present invention relates to optical medical field, and more particularly to an optical coherence tomography (OCT) system.

BACKGROUND ART

OCT is a method of interferometry that determines the scattering profile of a sample along the OCT beam. OCT systems can operate in the time domain (TD-OCT) or the frequency domain (FD-OCT). FD-OCT techniques have significant advantages in speed and signal-to-noise ratio as compared to TD-OCT. The spectral information discrimination in FD-OCT is typically accomplished by using a dispersive spectrometer in the detection arm in the case of spectral-domain OCT (SD-OCT) or rapidly scanning a swept laser source in the case of swept-source OCT (SS-OCT).

Figure 1:
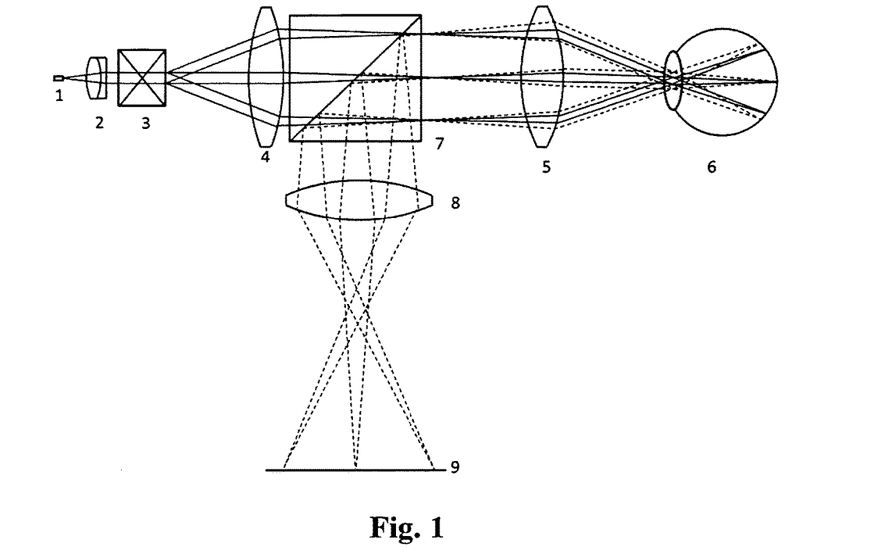
FIG. 1 shows a schematic view of the OCT system in the prior art for retinal scanning.

OCT systems have been used in the prior art to scan the retina of a patient so as to perform medical diagnosis. FIG. 1 shows an embodiment of an OCT scan module for scanning the retina of an eye in the prior art, the OCT scan module illustrated by FIG. 1 comprising fiber 1, collimator lens 2, X/Y scan-unit 3, retina scan lens 4, ocular lens 5, beam splitter 7, internal fixation lens 8 and internal fixation target 9. The solid-line-beam-path in FIG. 1 shows the OCT scan beam path in which a beam is focused on the retina of a patient's eye 6 under investigation to scan the eye 6. The beam can originate from any one of a variety of sources including broadband light sources with short temporal coherence lengths or swept laser sources and can be introduced into the OCT system via fiber 1. The dashed-line-beam-path in FIG. 1 shows the fixation beam path; the internal fixation target 9 is coupled to the OCT scan beam path via the internal fixation lens 8 and the beam splitter 7 and is then imaged on the retina of the eye 6 under investigation via the ocular lens 5 to define the viewing direction of the eye 6 under investigation during retinal scanning. Light scattered from the sample is collected, typically into the same fiber 1 used to route the light for illumination. Collected sample light is combined with reference light (not shown) to form light interference in a detector (not shown). The output from the detector is supplied to a processor (not shown). The results can be stored in the processor or displayed on a display. The processing and storing functions may be localized within the OCT instrument or functions may be performed on an external processing unit to which the collected data is transferred. This unit could be dedicated to data processing or perform other tasks which are quite general and not dedicated to the OCT device.

However, in daily diagnosis, it may be desired to use an OCT system to scan structures in the anterior segment of the eye of a patient such as the cornea. In order to use an OCT system to optionally achieve both retinal scanning and corneal scanning, in the prior art, the portion of the OCT system shown in FIG. 1 is varied to obtain the designs shown in FIGS. 2, 3 and 4.

Figure 2:
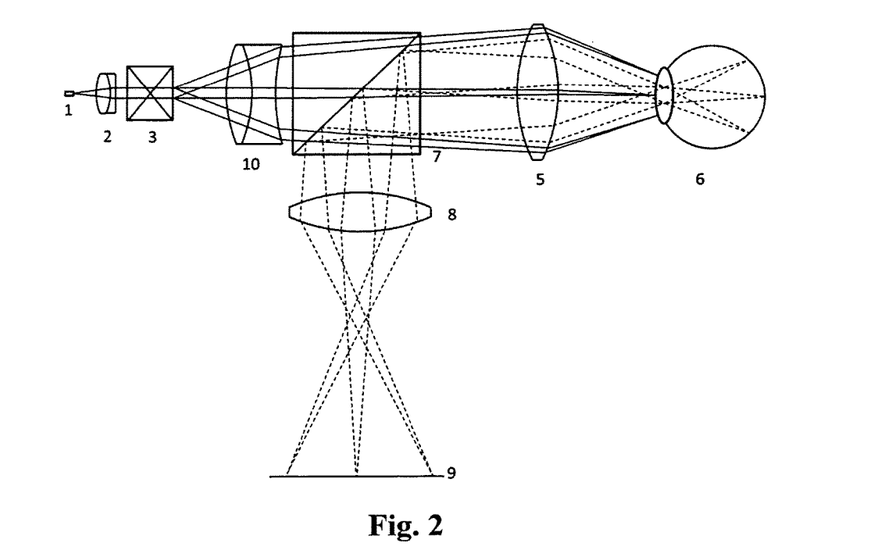
FIG. 2 schematically shows a varied OCT system in the prior art for retinal scanning.

As shown in FIG. 2, the retina scan lens 4 of the OCT system in FIG. 1 can be replaced with a anterior segment scan lens 10 to switch the OCT system from retinal scanning to anterior segment scanning (such as corneal scanning) without changing the fixation beam path. In order to realize the OCT system that can be used both for retinal scans and anterior segment scans as shown in FIG. 2, there is a need to provide the existing OCT system with additional optical-mechanical modules to exchange the retina scan lens 4 and the anterior segment scan lens 10 and to position different lenses precisely in the optical system of the OCT system and adjust the length of one of the reference arm and the sample arm to achieve the corresponding function. Thus complexity and cost of the instrument is greatly increased in order to achieve the function of anterior segment scanning. An example of such an OCT system is disclosed in U.S. Pat. No. US2007/0291277A1, the disclosures of which are hereby incorporated herein by reference as if set forth in their entirety.

Figure 3:
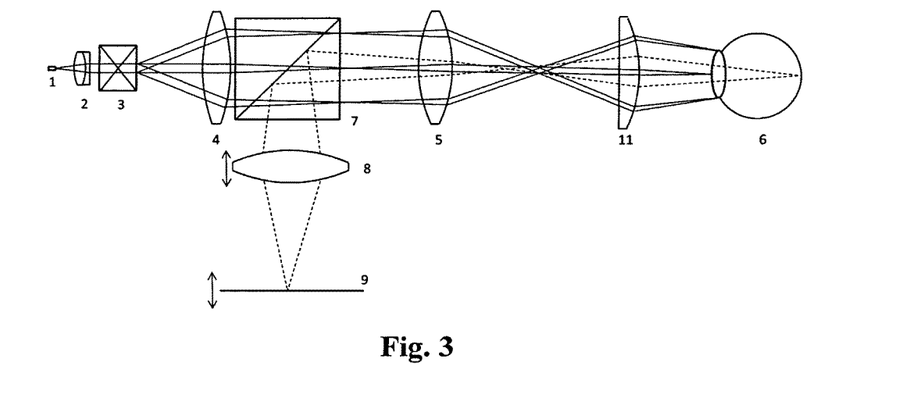
FIG. 3 schematically shows another varied OCT system in the prior art for retinal scanning.

Further as shown in FIG. 3, it is possible to add an anterior segment scan lens 11 externally to the ocular lens 5 of the OCT system of FIG. 1 for changing OCT beams from being focused on the retina to focus on the cornea. Due to addition of the anterior segment scan lens 11, the beams of the internal fixation beam path which were focused on the retina will also be focused on the cornea; preventing the eye under investigation from viewing the original internal fixation target 9 sharply anymore. This problem can be solved by adapting the positions of optical components and/or the fixation target in the internal fixation beam path, so as to re-focus the beams of the internal fixation beam path onto the retina of the eye under investigation, so that the eye under investigation can see the fixation target 9 clearly during anterior segment scanning. Adaptation to the position of the optical components and/or the fixation target is typically done by motors. Although the solution of FIG. 3 enables an existing OCT system for retinal scanning to scan a patient's cornea by arranging the anterior segment scan lens 11 externally to the ocular lens 5, it is necessary to adjust the internal fixation beam path to allow the eye under investigation to see the fixation target 9 clearly during anterior segment scan, so that complexity and cost of the instrument is still increased. An example of such an OCT system is disclosed in U.S. Pat. No. US2012/0140176A1, the disclosures of which are hereby incorporated herein by reference as if set forth in their entirety.

Figure 4:
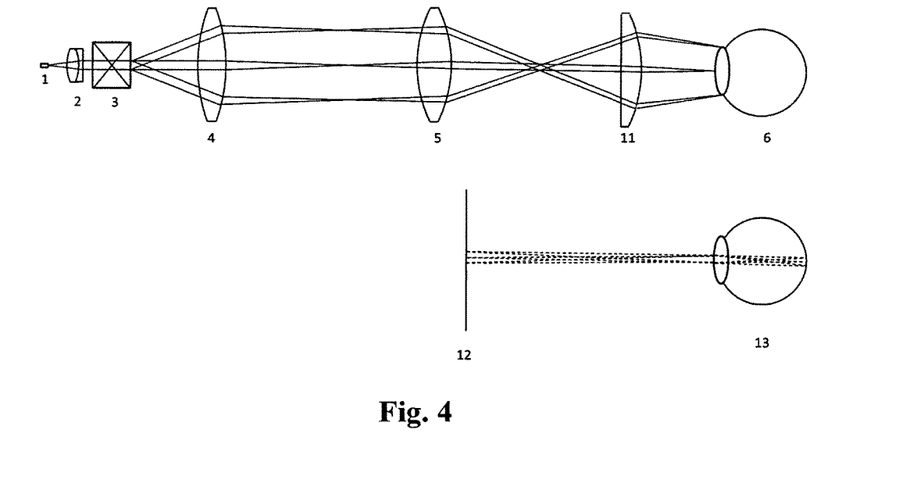
FIG. 4 schematically shows an external fixation target used in the prior art to define the viewing direction of the eye under investigation.

Furthermore, as shown in FIG. 4, an external fixation target 12 may be used. During the anterior segment scan, the patient is looking with the second eye 13 which is not under investigation by the OCT system, onto an external fixation target 12. Since both eyes of a human being share the same viewing direction, the viewing direction of the eye 6 under investigation can be defined by defining the viewing direction of the second eye 13. However, the solution shown in FIG. 4 does not work for patients who have only one functioning (seeing) eye. An example of such an external fixation target and relevant treatment method is disclosed in the document "SPECTRALIS Anterior Segment Module" obtainable from the web site "http://www.heidelbergengineering.com/international/wp-content/uploads/2012/03/SPECTRALIS-ASM_How-to-acquire-perfect-image_EN_web.pdf".

SUMMARY OF THE INVENTION

In order to solve the above problems, the present invention provides an OCT system comprising: an OCT scanning module for retinal scanning and an add-on anterior segment scan module which is attached externally to the OCT scan module for retinal scanning so as to switch the OCT system from retinal scan function to anterior segment scan function; the add-on anterior segment scan module comprises at least one anterior segment scan lens to focus the OCT scan beam onto the retina of an eye under investigation, and an add-on fixation target to maintain the viewing direction of the eye while carrying out anterior segment scan.

In a preferred embodiment, the add-on module is an independent separable module that can be directly attached to the exterior of the OCT scan module for retinal scanning.

In a preferred embodiment, the distance between the anterior segment scan lens and the add-on fixation target is adjustable. Preferably, adjustment of the distance between the anterior segment scan lens and the add-on fixation target can be done electrically or manually.

In a preferred embodiment, the anterior segment scan lens includes at least one singlet or doublet.

In a preferred embodiment, the anterior segment scan lens includes two independent singlets.

In a preferred embodiment, lateral (i.e. horizontal and vertical) positions of the add-on fixation target can be adjusted. Preferably, adjustment of the lateral (i.e. horizontal and vertical) positions of the add-on fixation target can be done electrically or manually.

In a preferred embodiment, the add-on fixation target is arranged within the OCT scanning beam path. Preferably, the add-on fixation target has a transparent central area to allow the OCT scan beam to pass.

In a preferred embodiment, the add-on anterior segment scan module further includes a beam splitter, and the add-on fixation target is arranged outside the OCT scan beam path and is coupled into the OCT scan beam path via the beam splitter. Preferably, the central area of the add-on fixation target has additional patterns. Preferably, the beam splitter is a beam splitter cube or a beam splitter plate.

In a preferred embodiment, the add-on fixation target is arranged on a transparent substrate.

In a preferred embodiment, the add-on fixation target is illuminated by a light source so that the add-on fixation target is visible to the eye under investigation.

In a preferred embodiment, the add-on fixation target is in some way illuminated so that the add-on fixation target is visible to the eye under investigation. Preferably, the add-on fixation target is arranged on the substrate by means of fluorescent paint.

In a preferred embodiment, the add-on fixation target is arranged on a flat surface, a curved or an aspheric surface.

Compared with the prior art, the OCT system of the present invention is advantageous because the add-on anterior segment scan module is attached externally to the existing OCT scan module for retinal scanning and has an add-on fixation target, so it is possible to keep the viewing direction of the eye under investigation while achieving anterior segment scanning without adjusting/changing the internal beam path and relevant structure of the existing OCT system. This is less complex and more cost effective than previous approaches, and the OCT system of the present invention can be adapted to patients with only one functioning eye.

DETAILED DESCRIPTION OF THE PREFERRED EMBODIMENTS

The following is a description of the OCT system of the present invention with reference to the drawings. Detailed depiction is provided below to fully understand the present invention. Nevertheless, it is obvious to those skilled in the art that the present invention can be achieved without some of the details. In addition, it shall be understood that the present invention is not limited to the depicted special embodiments. On the contrary, the following features and factors may be combined to carry out this invention, despite whether they relate to different embodiments. Therefore, the following aspects, features, embodiments and advantages shall only be construed as description but shall not be considered as limitations of the claims unless it is explicitly pointed in the claims. While the detailed description is focused on converting a retinal scanning OCT system to an anterior scanning OCT system, the idea would also apply to the opposite scenario, converting an anterior scanning OCT system to a retinal scanning system.

Figure 5:
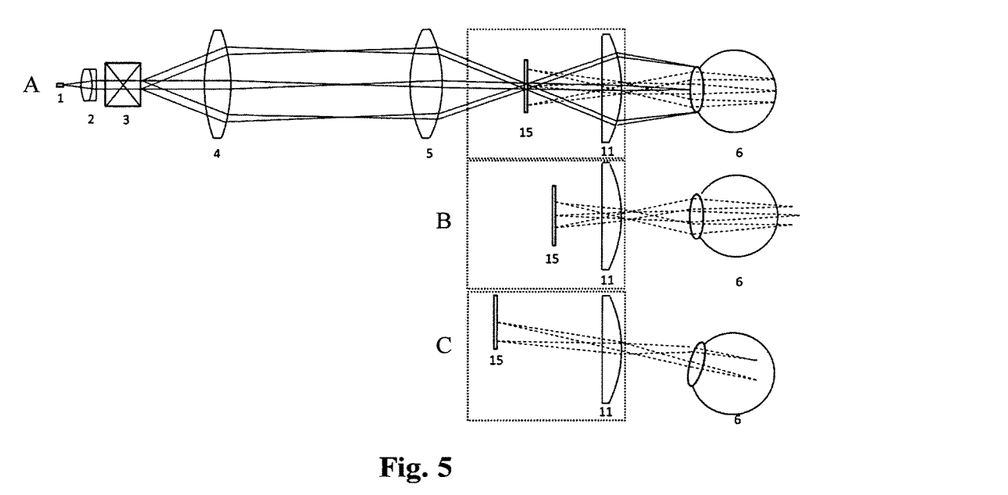
FIG. 5 shows a schematic view of an OCT system of an embodiment of the present invention for retinal scanning and anterior segment scanning.

FIG. 5 illustrates an embodiment of the present invention having an OCT scan module for retinal scanning with sub-system for anterior segment scanning. Besides conventional optical elements of the OCT scan module for retinal scanning, the OCT system shown in FIG. 5 comprises an add-on anterior segment scan module (three different examples of such a module are shown in the squares of FIG. 5) that can be attached to the exterior of the ocular lens 5, so as to switch from retinal scanning to anterior segment scanning. Preferably, after scanning is switched into anterior segment scanning, it is possible to enable the current internal fixation target in the OCT system for retinal scanning to be invisible to the eye under investigation (e.g. stopping illuminating the internal fixation target). The add-on anterior segment scan module includes anterior segment scan lens 11 which is used to change OCT beams from being focused on the retina to focus on structures in the anterior segment such as the cornea of the eye under investigation. The module also includes a fixation target 15 which is used to maintain the viewing direction of the eye under investigation while carrying out the anterior segment scan. The fixation target 15 may be a reticle with special patterns. The solid-line-beam-path in FIG. 5 shows an OCT scan beam path in which the OCT scan beams are focused on the anterior segment such as the cornea of the eye under investigation to scan the cornea. The dashed-line-beam-path in FIG. 5 shows the fixation beam path in which the fixation target 15 is focused onto the retina of the eye under investigation via the anterior segment scan lens 11 to form an image. In this way, it is possible to keep the eye under investigation gazing at the direction defined by the fixation target 15 so as to focus the OCT scan beams onto the anterior segment such as cornea of the eye and to scan the cornea.

Various means may be used to make the fixation target 15 visible to the patient. For example, a light source (e.g. LED, light bulb, display) can be used to illuminate the fixation target 15 or can be used directly as the fixation target 15 so that the fixation target 15 is visible to the patient. A window may be provided in the module, through which external light can illuminate the fixation target 15. Also, the fixation target 15 may be drawn or printed on the substrate (e.g. reticle) with fluorescent paint to make the fixation target 15 illuminate itself after being temporarily illuminated.

The fixation target may be achieved by various means, for example, a fixation target pattern drawn on a glass, crystal or plastic material, or a fixation target pattern directly shown by a display or may be an illuminated fixation target. If a display is used to directly create the fixation target pattern, the display can be placed at a fixation target position shown in FIG. 8, and the light emitted by the display is coupled to the OCT scan beam path via the beam splitter. In this case, lateral (i.e. horizontal and vertical) movement of the fixation target can be achieved by changing the display position of the fixation target on the electric display, without a mechanical structure to realize lateral movement of the fixation target.

Optionally, the distance between the fixation target 15 and the anterior segment scan lens 11 can be adjusted, and the lateral (i.e. horizontal and vertical) position of the fixation target 15 is adjustable as well. Specifically, row A of FIG. 5 shows anterior segment scanning for a normal eye, wherein the distance between the fixation target 15 and the anterior segment scan lens 11 and the lateral position of the fixation target 15 are in a standard state. In row B of FIG. 5, the distance between the anterior segment scan lens 11 and the fixation target 15 is adjusted to compensate refractive errors of the eye under investigation; specifically, the fixation target can be axially moved electrically or manually. In row C of FIG. 5, the lateral (i.e. horizontal and vertical) position of the fixation target 15 is adjusted to adjust viewing direction of the eye under investigation; specifically, the lateral (i.e. horizontal and vertical) position of the fixation target can be varied electrically or manually.

Figure 6:
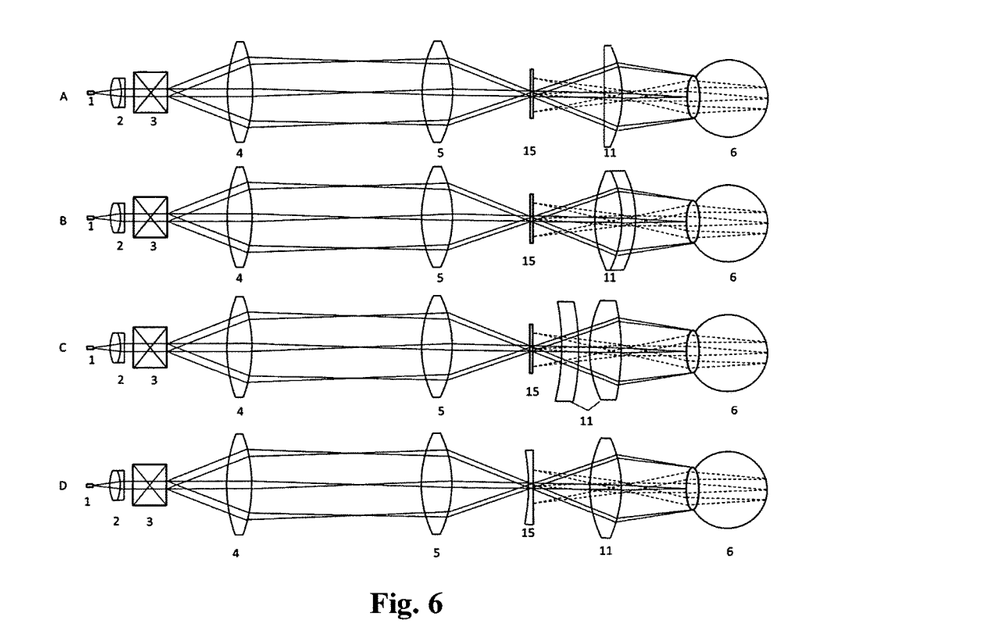
FIG. 6 schematically shows several varied OCT systems for retinal scanning and anterior segment scanning according to the present invention.

The anterior segment scan lens of the add-on anterior segment scan module of the OCT system for retinal scanning and anterior segment scanning in the present invention may include various kinds of lenses. In addition, the fixation target 15 can be arranged on a flat surface, a curved or aspheric surface as needed. FIG. 6 shows several variations of the OCT sub-system for anterior segment scanning of the present application. Specifically, for example, as shown by row A in FIG. 6, the anterior segment scan lens 11 may include a singlet. For example, as shown in row B of FIG. 6, the anterior segment scan lens 11 may include a doublet. For instance, as shown in row C of FIG. 6, the anterior segment scan lens 11 may include a lens group composed of two individual singlets. For example, the fixation target 15 may be arranged on a curve surface as shown in row D of FIG. 6.

Figure 7:
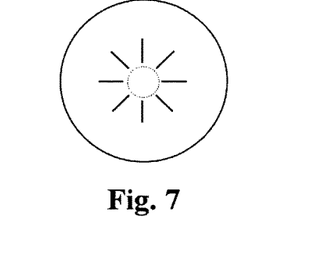
FIG. 7 shows a schematic view of a fixation target of the OCT system of an embodiment of the present invention for retinal scanning and anterior segment scanning.

The fixation target 15 of the invention may be provided with various patterns. FIG. 7 shows a pattern that can be adopted by the fixation target illustrated in FIGS. 5 and 6. The fixation target pattern is a plurality of (e.g. eight) radial lines equally distributed over the periphery of the transparent central area. The transparent central area ensures unblocked passage of the OCT scan beam. The transparent central area can be realized by a transparent substrate or an aperture disposed in the substrate. When the fixation target pattern in FIG. 7 is realized by central perforation in a non-transparent substrate, the fixation target will significantly block desired backscattered light from the anterior segment. Blocking can be avoided by using a transparent substrate.

Figure 8:
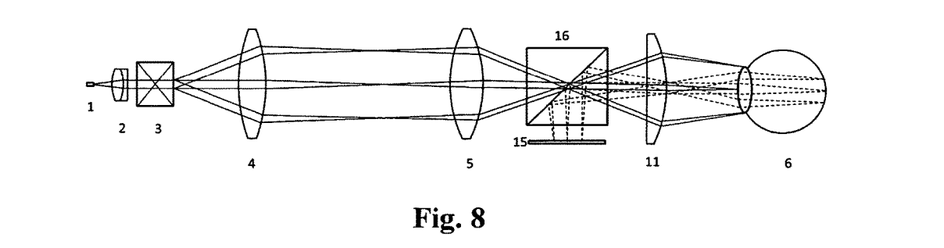
FIG. 8 shows a schematic view of an OCT system of another embodiment of the present invention for retinal scanning and anterior segment scanning.
Figure 9:
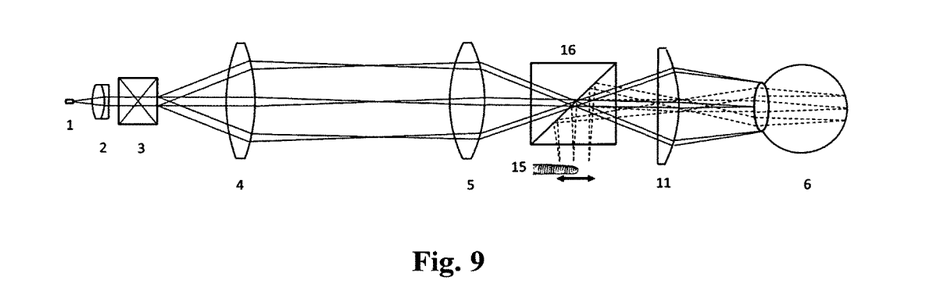
FIG. 9 shows a schematic view of an OCT system of FIG. 8 where the fixation target is replaced by the ophthalmologist's finger.

FIG. 8 shows a schematic view of another embodiment of the OCT system for retinal scanning and anterior segment scanning sub-module of the present invention. Unlike FIG. 5, the image of the fixation target 15 of FIG. 8 is coupled to the OCT scan beam path via a beam splitter 16 which may be a beam splitter cube, a beam splitter plate, or a beam splitter pellicle. In this case, the fixation target 15 may be integral to the add-on anterior segment scan module, or may be provided externally. When the fixation target 15 is provided externally, the fixation target may be supplied, for example, by the operator holding up a hand to look at; or for a second example, supplied by a portion of the instrument, such as by placing the external fixation target originally for second eye fixation (the eye that is not under investigation) and providing fixation view for $1^{st}$ eye (the eye under investigation) via beam splitter 16. In such configuration, the ophthalmologist's finger could also be placed and act as the fixation target. In such a way, the patient's eye could follow the movement of ophthalmologist's finger if necessary as illustrated in FIG. 9.

Figure 10:
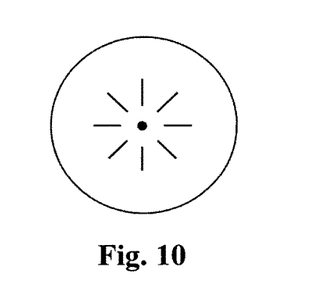
FIG. 10 shows a schematic view of a fixation target of the OCT system of another embodiment of the present invention for retinal scanning and anterior segment scanning.

FIG. 10 illustrates a possible pattern that can be used by the fixation target of FIG. 8. The central area of the fixation target of FIG. 10 may have additional patterns, such as a solid dot. Of course, the fixation target in FIG. 8 may adopt a fixation target pattern having no additional patterns at the central area.

In the OCT system for retinal scanning and anterior segment scanning described in the present application, it is possible to carry out anterior segment scanning without adjusting/changing the internal beam path of the OCT system, and simultaneously to provide a target for gaze fixation to the eye under investigation to maintain viewing direction; therefore the cost of production is saved according to the OCT system in the present invention, and it is also well adapted to the patients with only one functioning eye.

The present invention is disclosed with above preferred embodiments, however, it is not limited to these embodiments. Any variation and modifications made by any skilled person without departing from the spirit and principle of this invention are encompassed within the protection scope of the present invention. Therefore, the protection scope of the invention shall be defined by the attached claims.

The invention claimed is:

1. An OCT system, comprising an OCT scan module for retinal scanning, having an OCT scan beam, said system further comprising an anterior segment scan module which is attached externally to the OCT scan module for retinal scanning so as to switch between retinal scanning function and anterior segment scanning function of the OCT system;

the anterior segment scan module comprising:
   at least one anterior segment scan lens to focus the OCT scan beam in the anterior segment of an eye under investigation; and
   a fixation target to maintain the viewing direction of the eye during anterior segment scanning.

2. The OCT system according to claim 1, wherein the add-on anterior segment scan module is an independent separable module that can be directly attached to the exterior of the OCT scan module for retinal scanning.

3. The OCT system according to claim 1, wherein the distance between the anterior segment scan lens and the fixation target is adjustable.

4. The OCT system according to claim 3, wherein the adjustment of the distance between the anterior segment scan lens and the fixation target can be done electrically or manually.

5. The OCT system according to claim 1, wherein the anterior segment scan lens include at least one singlet or doublet.

6. The OCT system according to claim 1, wherein the anterior segment scan lens include two individual singlets.

7. The OCT system according to claim 1, wherein the lateral positions of the fixation target can be adjusted.

8. The OCT system according to claim 7, wherein the adjustment of the lateral positions of the fixation target can be done electrically or manually.

9. The OCT system according to claim 1, wherein the fixation target is arranged along the OCT scanning beam path.

10. The OCT system according to claim 1, wherein the fixation target is a plurality of radial lines equally distributed over the periphery of the central area.

11. The OCT system according to claim 9, wherein the fixation target has a transparent area to allow the OCT scan beam to pass.

12. The OCT system according to claim 11, wherein the central area of the fixation target is transparent.

13. The OCT system according to claim 1, wherein the anterior segment scan module further includes a beam splitter, and the fixation target is arranged outside the OCT scan beam path and is coupled into the OCT scan beam path via the beam splitter.

14. The OCT system according to claim 13, wherein the central area of the fixation target has patterns.

15. The OCT system according to claim 14, wherein said patterns include a solid dot.

16. The OCT system according to claim 13, wherein the beam splitter is one of: a beam splitter cube, a beam splitter plate, or a beam splitter pellicle.

17. The OCT system according to claim 13, wherein the fixation target is provided externally of the anterior segment module.

18. The OCT system according to claim 1 wherein the fixation target is generated by a display.

19. The OCT system according to claim 1 wherein the fixation target is arranged on a transparent substrate.

20. The OCT system according to claim 1 wherein the fixation target is illuminated by a light source so that the fixation target is visible to the eye under investigation.

21. The OCT system according to claim 1 wherein the fixation target is self-illuminated so that the fixation target is visible to the eye under investigation.

22. The OCT system according to claim 21 wherein the fixation target is defined by fluorescent paint applied to a transparent substrate.

23. The OCT system according to claim 1 wherein the fixation target is arranged on one of: a flat, a curved, or an aspheric surface.

* * * * *

UNITED STATES PATENT AND TRADEMARK OFFICE
CERTIFICATE OF CORRECTION

PATENT NO. : 10,085,638 B2  
APPLICATION NO. : 14/908256  
DATED : October 2, 2018  
INVENTOR(S) : Martin Peschka et al.

Page 1 of 1

It is certified that error appears in the above-identified patent and that said Letters Patent is hereby corrected as shown below:

On the Title Page

In item (71), in Column 1, in "Applicant", Line 1, before "CARL ZEISS MEDITEC AG,"
insert -- CARL ZEISS MEDITEC, INC., Dublin, CA (US); --.

Signed and Sealed this
Eighth Day of January, 2019

Andrei Iancu
*Director of the United States Patent and Trademark Office*